(12) United States Patent
Peters et al.

(10) Patent No.: US 9,845,510 B2
(45) Date of Patent: Dec. 19, 2017

(54) COMPOSITIONS AND METHODS FOR RAPID DETECTION OF *SALMONELLA*

(71) Applicant: ENVIROLOGIX INC., Portland, ME (US)

(72) Inventors: Lars E. Peters, Portland, ME (US); Vikrant Dutta, Portland, ME (US); Thomas Guerrette, Portland, ME (US); Stephen A. Judice, Portland, ME (US); Breck O. Parker, Portland, ME (US)

(73) Assignee: ENVIROLOGIX INC., Portland, ME (US)

( * ) Notice: Subject to any disclaimer, the term of this patent is extended or adjusted under 35 U.S.C. 154(b) by 0 days.

(21) Appl. No.: 14/997,274

(22) Filed: Jan. 15, 2016

(65) Prior Publication Data
US 2016/0222440 A1 Aug. 4, 2016

Related U.S. Application Data

(63) Continuation of application No. PCT/US2015/027036, filed on Apr. 22, 2015.

(60) Provisional application No. 62/110,268, filed on Jan. 30, 2015.

(51) Int. Cl.
C07H 21/02 (2006.01)
C07H 21/04 (2006.01)
C12Q 1/68 (2006.01)

(52) U.S. Cl.
CPC .................................. *C12Q 1/689* (2013.01)

(58) Field of Classification Search
None
See application file for complete search history.

(56) References Cited

U.S. PATENT DOCUMENTS

2011/0223598 A1 9/2011 Opdyke et al.
2013/0059290 A1 3/2013 Armes

OTHER PUBLICATIONS

Genbank: FX120945.2 [Calophyllum inophyllym mRNA, contig: CI_04849, mRNA sequence), [retrieved on Oct. 1, 2015 from http://ncbi.nlm.nih.gov/nuccore/FX120945] May 17, 2014 (May 17, 2014) entire doc.
International Search Report and Written Opinion, issued in corresponding PCT/US2015/027036, filed on Apr. 22, 2015, (13 pages).

*Primary Examiner* — Young J Kim
(74) *Attorney, Agent, or Firm* — Melissa Hunter-Ensor; Elbert Chiang; Greenberg Traurig, LLP

(57) ABSTRACT

The present invention features rapid and accurate methods for detecting *Salmonella* (e.g., in a food product, environmental sample, biological sample or other material).

5 Claims, 7 Drawing Sheets

FIG. 1 Sequence in 5'-3' Direction of the "invA" Gene from *Salmonella enterica*.

TTATATTGTTTTTATAACATTCACTGACTTGCTATCTGCTATCTCACCGAAAGATAAAACCTCCAGATCCGGAAAACGACCTTCAATCA
TTTTCTTAATAAATCGACGGACATCGACAGACGTAAGGAGGACAAGATCTTTATGTGCAATCAATAAATCATCCAACTTAAGTGTAATG
AGATCCATCAAATTAGCGGAGGCTTCCGGGTCAAGGCTGAGGAAGGTACTGCCAGAGGTCTGACGGATCCCTTTGCGAATAACATCCTC
AACTTCAGCAGATACCATTACTGCTCGTAATTCGCCGCCATTGGCGAATTTATGACAAATATAACGCGCCATTGCTCCACGAATATGCT
CCACAAGGTTAATGACATCTTTTTCTCTTGGCGCCCACAATGCGAGCGCTTCCATAATTAACTTCATATTACGCACGGAAACACGTTCG
CTTAACAAACGCTGCAAAACTTCAGATATACGTTGTACCGTGGCATGTCTGAGCACTTCTTTAAGTAAATCAGGAAATTTCGCTTCCAG
TTGGTCCAGCATATGTTTTGTTTCCTGAATACCGAAATATTCATTGACGTTGCGCGCCAGCGTCACCGCCAGACAGTGGTAAAGCTCAT
CAAGCGCGTTCCGCAACACATAGCCAAGCTCCCGGAGTTTCTCCCCCTCTTCATGCGTTACCCAGAAATACTGACTGCTACCTTGCTGA
TGGATTGTTGGATTAATACCAAAGGACACGACTTCATCGGAATAATTTACCACTCGCATCAAATCAAAATAGACCGTAAATTGTTCAAC
ACGGATCTCATTAATCAACAATACGATGCTGTTATCGTCCAGGCCCTCGCCATCGCGTAACAATACTTCCGGCAGGCGCACGCCATAAT
CAATAAAGAACTGACTACGTAGACGCTCCGCAAGTTGAGCTTTTTCCAGATCTTCACGCCGGCTCTTCGGCACAAGTAATATCAACGGT
ACGGTCTCTGTAGAGACTTTATCGAGATCGCCAATCAGTCCTAACGACGACCCTTCTTTTTCCTCAATACTGAGCGGCTGCTCGCCTTT
GCTGGTTTTAGGTTTGGCGGCGCTACGTTTTGCTTCACGGAATTTAAAATAGAAGAGTACGCTTAAAACCACCGATAAAATAACAAAAA
CCGGCAGTGGGAATCCCGGCAGAGTTCCCATTGAAATGGTCAAAATAGCCGTAACAACCAATACAAATGGGTTGTTCAACAGCTGCGTC
ATGATATTCCGCCCCATATTATCGCTATCGCCATTTACGCGGGTCACGATAAAACCGGCACTAATCGCAATCAACAATGCGGGGATCTG
GGCGACAAGACCATCACCAATGGTCAGCATGGTATAAGTAGACAGGGCGGAGGACAAATCCATACCATGGCGAGTCATCCCCACCGAAA
TACCGCCAATAAAGTTCACAAAGATAATAATGATGCCGGCAATAGCGTCACCTTTGATAAACTTCATCGCACCGTCAAAGGAACCGTAA
AGCTGGCTTTCCCTTTCCAGTACGCTTCGCCGTTCGCGCGCGGCATCCGCATCAATAATACCGGCCTTCAAATCGGCATCAATACTCAT
CTGTTTACCGGGCATACCATCCAGAGAAAATCGGGCCGCGACTTCCGCGACACGTTCTGAACCTTTGGTAATAACGATAAACTGGACCA
CGGTGACAATAGAGAAGACAACAAAACCCACCGCCAGGCTATCGCCAATAACGAATTGCCCGAACGTGGCGATAATTTCACCGGCATCG
GCTTCAATCAAGATAAGACGACTGGTACTGATCGATAATGCCAGACGAAAGAGCGTGGTAATTAACAGTACCGCAGGAAACGTTGAAAA
ACTGAGGATTCTGTCAATGTAGAACGACCCCATAAACACCAATATCGCCAGTACGATATTCAGTGCGATCAGGAAATCAACCAGATAGG
TAGGTAATGGAATGACGAACATAGAAATGATCATCACCATTAGTACCAGAATCAGTAATTCAGGTCGTAAACGAGCACTGTTAAGTAGA
GAAAGCAGCAC

FIG. 2 Primer and Probe Sequences of "invA" Target Sequence Region I

Forward Primers

5'-TGACTCCATATGGAGTCACATCACmCGAAATACmCmGmCmCmA-3'

5'-GACTCGATATCGAGTCTTTCCACmCGAAATACmCmGmCmCmA-3'*

5'-GAAAGACTCGCGAGTCTTTCCACmCGAAATACmCmGmCmCmA-3'

Reverse Primers

5'-TGACTCCATATGGAGTCACATCGGmCATCATTATTATCTTTGmUmGmAmAmC-3'

5'-GACTCGATATCGAGTCTTTCCGGmCATCATTATTATCTTTGmUmGmAmAmC-3'*

5'-GAAAGACTCGCGAGTCTTTCCGGmCATCATTATTATCTTTGmUmGmAmAmC-3'

Bases labeled red and with the prefix "m" indicate the position of 2'-O-methyl ribonucleotides.

"Molecular Beacon" Detection Probe

5'-CalRed$_{610nm}$-CGCCTGTGAACTTTATTGGCG-BHQ2-3'*

FIG. 3 Primer and Probe Sequences of "invA" Target Sequence Region II

Forward Primers

5'–TGACTCCATATGGAGTCACATATACTCATCTGTmUmAmCmC–3'

5'–mUGCCGACTCGCGAGTCGGCAATACTCATCTGTmUmAmCmC–3'

5'–mGGCTGACTCCTGCAGGAGTCAGCCATACTCATCTGTTmUmAmCmC–3'

5'–mCAGGGACTCCCGGGAGTCGCTGATACTCATCTGTTmUmAmCmC–3'

Reverse Primer

5'–TGACTCCATATGGAGTCACATTTTTCTCTGGmAmUmGmG–3'

5'–mUGCCGACTCGCGAGTCGGCATTTTCTCTGGmAmUmGmG–3'

5'–mGGCTGACTCCTGCAGGAGTCAGCCTTTTCTCTGGmAmUmGmG–3'

5'–mCAGGGACTCCCGGGAGTCGCTGTTTTCTCTGGmAmUmGmG–3'

Bases labeled red and with the prefix "m" indicate the position of 2'-O-methyl ribonucleotides.

"Molecular Beacon" Detection Probe

5'–CalRed$_{610nm}$–ACCTGTTTACCGGGCATACAAACAGGT–BHQ2–3'

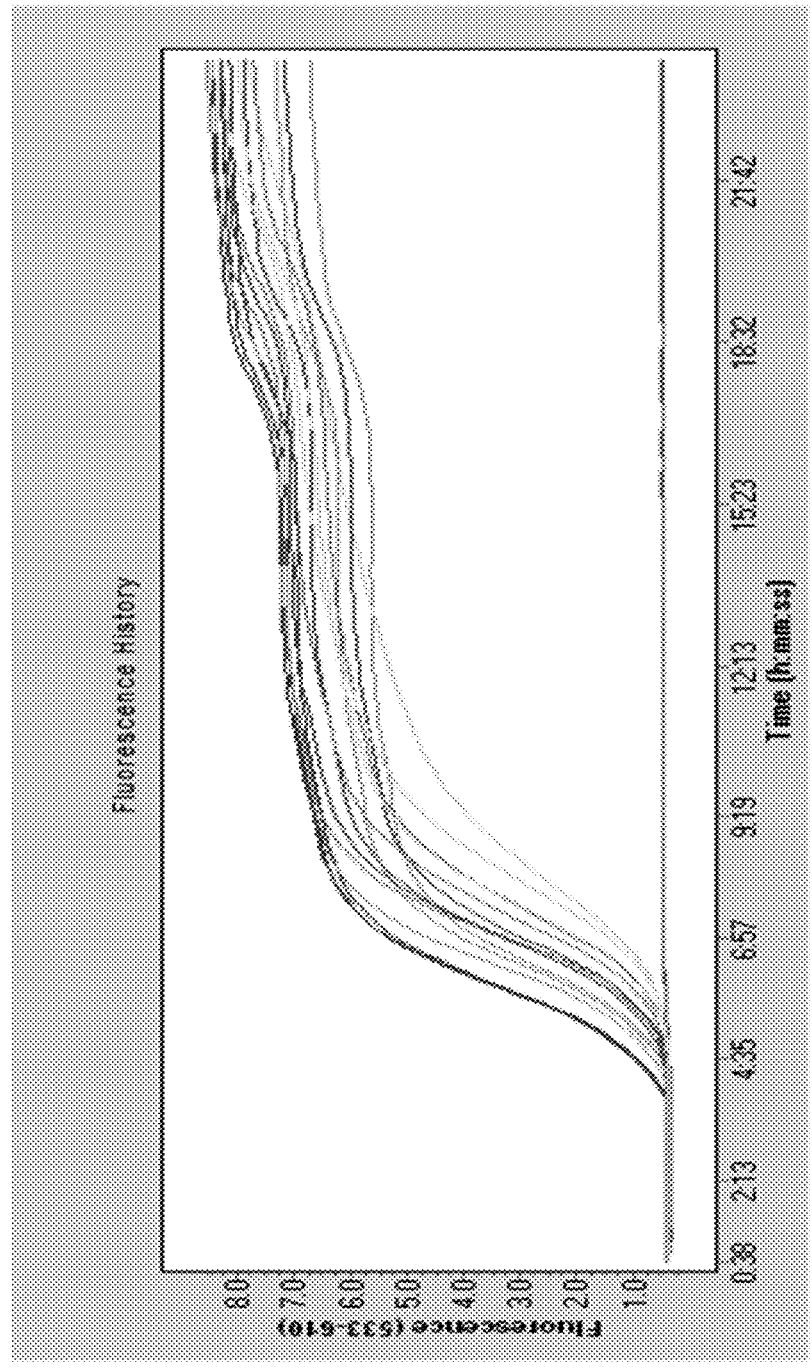
FIG. 4  Analytical Limit of Detection (ALOD) of *Salmonella enterica* "invA" Region I DNAble Assay

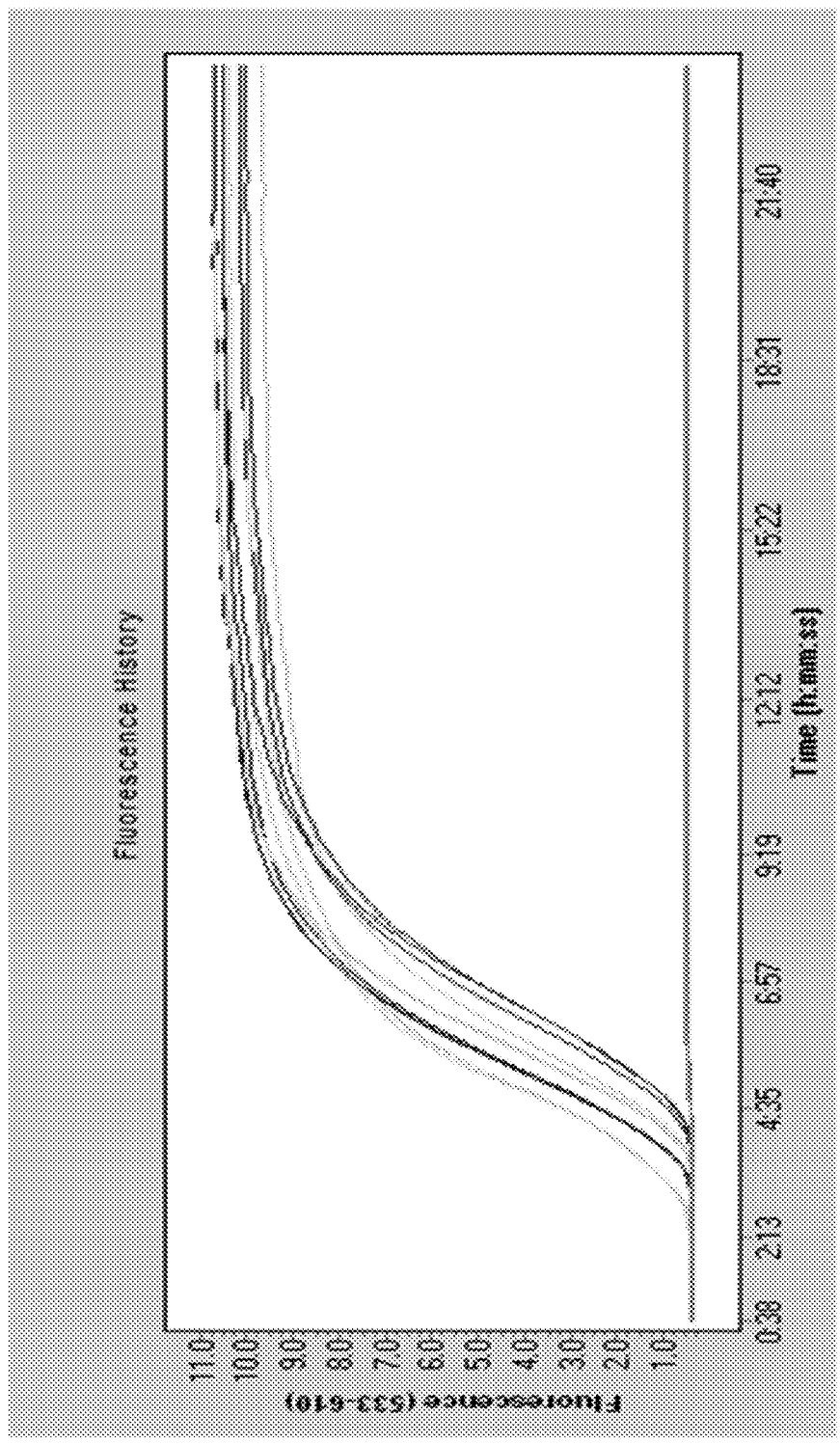
FIG. 5 Biological Limit of Detection (BLOD) of *Salmonella enterica* "invA" Region I DNAble Assay FIG. 6 Comparing the LOD on *Salmonella enterica* gDNA between commercial NEAR assay targeting "invA" and the novel isothermal Salmonella "invA" assay.

FIG. 6 Comparing the LOD on *Salmonella enterica* gDNA between commercial NEAR assay targeting "invA" and the novel isothermal Salmonella "invA" assay.

SEQUENCE LISTING

<160> NUMBER OF SEQ ID NOS: 22

<210> SEQ ID NO 1
<211> LENGTH: 46
<212> TYPE: DNA
<213> ORGANISM: Salmonella enterica

<400> SEQUENCE: 1
caccgaaata ccgccaataa agttcacaaa gataataatg atgccg        46

<210> SEQ ID NO 2
<211> LENGTH: 38
<212> TYPE: DNA
<213> ORGANISM: Salmonella enterica

<400> SEQUENCE: 2
atactcatct gtttaccggg cataccatcc agagaaaa        38

-continued

```
<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gactcgatat cgagtctttc caccgaaata ccgcca                               36

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 4
gactcgatat cgagtctttc cggcatcatt attatctttg ugaac                     45

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cgcctgtgaa ctttattggc g                                               21

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgactccata tggagtcaca tcaccgaaat accgcca                              37

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaaagactcg cgagtctttc caccgaaata ccgcca                               36

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 8
tgactccata tggagtcaca tatactcatc tgttuacc                              38

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 9
ugccgactcg cgagtcggca atactcatct gttuacc                               37

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 10
ggctgactcc tgcaggagtc agccatactc atctgttuac c                          41

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 11
cagcgactcc cgggagtcgc tgatactcat ctgttuacc                             39

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 12
tgactccata tggagtcaca tcggcatcat tattatcttt gugaac                     46

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 13
gaaagactcg cgagtctttc cggcatcatt attatctttg ugaac         45

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 14
tgactccata tggagtcaca tttttctctg gaugg                    35

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 15
ugccgactcg cgagtcggca ttttctctgg augg                     34

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 16
ggctgactcc tgcaggagtc agccttttct ctggaugg                 38

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 17
cagcgactcc cgggagtcgc tgttttctct ggaugg                   36

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 18
acctgtttac cgggcataca aacaggt                                              27

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(12)
<223> OTHER INFORMATION: a, c, t, g, unknown or other

<400> SEQUENCE: 19
gagtcnnnnn nn                                                              12

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 20 ggatcnnnnn                                                                 10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 21 gagtcnnnnn                                                                 10

<210> SEQ ID NO 22
<211> LENGTH: 2058
<212> TYPE: DNA
<213> ORGANISM: Salmonella enterica

<400> SEQUENCE: 22
ttatattgtt tttataacat tcactgactt gctatctgct atctcaccga aagataaaac          60
ctccagatcc ggaaaacgac cttcaatcat tttcttaata aatcgacgga catcgacaga         120
cgtaaggagg acaagatctt tatgtgcaat caataaatca tccaacttaa gtgtaatgag         180
atccatcaaa ttagcggagg cttccgggtc aaggctgagg aagtactgc cagaggtctg          240 acggatccct tgcgaataa catcctcaac ttcagcagat accattactg ctcgtaattc          300
gccgccattg gcgaatttat gacaaatata cgcgccatt gctccacgaa tatgctccac          360
aaggttaatg acatctttt ctcttggcgc ccacaatgcg agcgcttcca taattaactt         420
catattacgc acggaaacac gttcgcttaa caaacgctgc aaaacttcag atatacgttg        480

```
taccgtggca tgtctgagca cttctttaag taaatcagga aatttcgctt ccagttggtc    540
cagcatatgt tttgtttcct gaataccgaa atattcattg acgttgcgcg ccagcgtcac    600
cgccagacag tggtaaagct catcaagcgc gttccgcaac acatagccaa gctcccggag    660
tttctccccc tcttcatgcg ttacccagaa atactgactg ctaccttgct gatggattgt    720
tggattaata ccaaaggaca cgacttcatc ggaataattt accactcgca tcaaatcaaa    780
atagaccgta aattgttcaa cacggatctc attaatcaac aatacgatgc tgttatcgtc    840
caggccctcg ccatcgcgta acaatacttc cggcaggcgc acgccataat caataaagaa    900
ctgactacgt agacgctccg caagttgagc tttttccaga tcttcacgcc ggctcttcgg    960
cacaagtaat atcaacggta cggtctctgt agagacttta tcgagatcgc caatcagtcc   1020
taacgacgac ccttctttt cctcaatact gagcggctgc tcgcctttgc tggttttagg    1080
tttgcggcg ctacgttttg cttcacggaa tttaaaatag aagagtacgc ttaaaaccac    1140
cgataaaata acaaaaaccg gcagtgggaa tcccggcaga gttcccattg aaatggtcaa   1200
aatagccgta acaaccaata caaatgggtt gttcaacagc tgcgtcatga tattccgccc   1260
catattatcg ctatcgccat ttacgcgggt cacgataaaa ccggcactaa tcgcaatcaa   1320
caatgcgggg atctgggcga caagaccatc accaatggtc agcatggtat aagtagacag   1380
ggcggaggac aaatccatac catggcgagt catccccacc gaaataccgc caataaagtt   1440
cacaaagata ataatgatgc cggcaatagc gtcacctttg ataaacttca tcgcaccgtc   1500
aaaggaaccg taaagctggc tttccctttc cagtacgctt cgccgttcgc gcgcggcatc   1560
cgcatcaata ataccggcct tcaaatcggc atcaatactc atctgtttac cgggcatacc   1620
atccagagaa aatcgggccg cgacttccgc gacacgttct gaaccttttgg taataacgat   1680
aaactggacc acggtgacaa tagagaagac aacaaaaccc accgccaggc tatcgccaat   1740
aacgaattgc ccgaacgtgg cgataatttc accggcatcg gcttcaatca agataagacg   1800
actggtactg atcgataatg ccagacgaaa gagcgtggta attaacagta ccgcaggaaa   1860
cgttgaaaaa ctgaggattc tgtcaatgta gaacgacccc ataaacacca atatcgccag   1920
tacgatattc agtgcgatca ggaaatcaac cagataggta ggtaatggaa tgacgaacat   1980
agaaatgatc atcaccatta gtaccagaat cagtaattca ggtcgtaaac gagcactgtt   2040
aagtagagaa agcagcac                                                 2058
```

COMPOSITIONS AND METHODS FOR RAPID DETECTION OF SALMONELLA

CROSS-REFERENCE TO RELATED APPLICATION

This application is a continuation under 35 U.S.C. §120 of PCT international application Serial No. PCT/US2015/027036, filed Apr. 22, 2015, designating the United States and published in English, which claims priority to and the benefit of U.S. Provisional Patent Application Ser. No. 62/110,268, filed Jan. 30, 2015. The entire contents of each of these applications is hereby incorporated by reference herein.

SEQUENCE LISTING

The instant application contains a Sequence Listing which has been submitted electronically in ASCII format and is hereby incorporated by reference in its entirety. Said ASCII copy, created on Jan. 15, 2016, is named 049224.1050US1 (00124)_SL.txt and is 8,913 bytes in size.

BACKGROUND OF THE INVENTION

*Salmonella* is one of the most common pathogens of foodborne disease worldwide. It is responsible for a large number of infections in both humans and animals. In fact, *Salmonella* causes approximately 93.8 million human infections and 155,000 deaths annually worldwide. *Salmonella* infections have been associated with eating foods, such as meat, eggs and fresh produce, contaminated with animal or human feces. The main causes of *Salmonella* illness are poultry and eggs. Recognizing the importance of preventing the spread of *Salmonella*, in 2014 the US FDA challenged US scientists to develop improved methods for detecting *Salmonella*. Current methods for detecting *Salmonella* in food products is difficult, expensive and time-consuming. Rapid and accurate detection methods are urgently required to prevent *Salmonella* contaminated food products from entering the animal or human food chain.

SUMMARY OF THE INVENTION

As described below, the present invention features rapid and accurate methods for detecting *Salmonella* (e.g., in a food product, environmental sample, biological sample or other material).

In one aspect, the invention features a method of detecting *Salmonella* in a sample, the method involving contacting a sample with forward and reverse primers that specifically bind a *Salmonella* nucleic acid molecule in the presence of a nicking enzyme, dNTPs, a detectable probe and a polymerase under conditions permissive for the isothermal amplification of the nucleic acid molecule, and detecting a *Salmonella* amplicon in the sample, where the method detects one of the following target sequences:

```
                                           (SEQ ID NO: 1)
5'-CACCGAAATACCGCCAATAAAGTTCACAAAGATAATAATGATGCCG-
3'
```
or
```
                                           (SEQ ID NO: 2)
5'-ATACTCATCTGTTTACCGGGCATACCATCCAGAGAAAA-3'.
```

In another aspect, the invention features a method for detecting *Salmonella* in a sample, the method involving contacting the sample with forward and reverse primers having the following sequences, respectively:

```
                                           (SEQ ID NO: 3)
5'GACTCGATATCGAGTCTTTCCACmCGAAATACmCmGmCmCmA 3'

(SEQ ID NO: 4)
5'GACTCGATATCGAGTCTTTCCGGmCATCATTATTATCTTTGmUmGmAm
AmC 3'
``` in the presence of a Nt.BstNBI(NEB) nicking enzyme, dNTPs, a Bst DNA polymerase I, and a detectable probe having the following sequence:

```
                                           (SEQ ID NO: 5)
               5' CGCCTGTGAACTTTATTGGCG 3';
``` and detecting the presence or absence of a *Salmonella* amplicon, where the presence of the *Salmonella* amplicon identifies *Salmonella* in the sample.

In another aspect, the invention features a primer selected from the following forward primers:

```
                                           (SEQ ID NO: 6)
5'-TGACTCCATATGGAGTCACATCACmCGAAATACmCmGmCmCmA-3'

(SEQ ID NO: 3)
5'-GACTCGATATCGAGTCTTTCCACmCGAAATACmCmGmCmCmA-3'

(SEQ ID NO: 7)
5'-GAAAGACTCGCGAGTCTTTCCACmCGAAATACmCmGmCmCmA-3'

(SEQ ID NO: 8)
5'-TGACTCCATATGGAGTCACATATACTCATCTGTTmUmAmCmC-3'

(SEQ ID NO: 9)
5'-mUGCCGACTCGCGAGTCGGCAATACTCATCTGTTmUmAmCmC-3'

(SEQ ID NO: 10)
5'-mGGCTGACTCCTGCAGGAGTCAGCCATACTCATCTGTTmUmAmCmC-
3'

(SEQ ID NO: 11)
5'-mCAGCGACTCCCGGGAGTCGCTGATACTCATCTGTTmUmAmCmC-3'
``` and reverse primers:

```
                                           (SEQ ID NO: 12)
5'-TGACTCCATATGGAGTCACATCGGmCATCATTATTATCTTTGmUmGm
AmAmC-3'

(SEQ ID NO: 4)
5'-GACTCGATATCGAGTCTTTCCGGmCATCATTATTATCTTTGmUmGm
AmAmC-3'

(SEQ ID NO: 13)
5'-GAAAGACTCGCGAGTCTTTCCGGmCATCATTATTATCTTTGmUmGm
AmAmC-3'

(SEQ ID NO: 14)
5'-TGACTCCATATGGAGTCACATTTTTCTCTGGmAmUmGmG-3'

(SEQ ID NO: 15)
5'-mUGCCGACTCGCGAGTCGGCATTTTCTCTGGmAmUmGmG-3'

(SEQ ID NO: 16)
5'-mGGCTGACTCCTGCAGGAGTCAGCCTTTTCTCTGGmAmUmGmG-3'

(SEQ ID NO: 17)
5'-mCAGCGACTCCCGGGAGTCGCTGTTTTCTCTGGmAmUmGmG-3',
``` where "m" indicates the position of a modification.

In another aspect, the invention features a pair of primers containing a forward and a reverse primer selected from forward primers (SEQ ID NO: 6)
5'-TGACTCCATATGGAGTCACATCACmCGAAATACmCmGmCmCmA-3'

(SEQ ID NO: 3)
5'-GACTCGATATCGAGTCTTTCCACmCGAAATACmCmGmCmCmA-3'

(SEQ ID NO: 7)
5'-GAAAGACTCGCGAGTCTTTCCACmCGAAATACmCmGmCmCmA-3'

(SEQ ID NO: 8)
5'-TGACTCCATATGGAGTCACATATACTCATCTGTTmUmAmCmC-3'

(SEQ ID NO: 9)
5'-mUGCCGACTCGCGAGTCGGCAATACTCATCTGTTmUmAmCmC-3'

(SEQ ID NO: 10)
5'-mGGCTGACTCCTGCAGGAGTCAGCCATACTCATCTGTTmUmAmCmC-3'

(SEQ ID NO: 11)
5'-mCAGCGACTCCCGGGAGTCGCTGATACTCATCTGTTmUmAmCmC-3' and reverse primers:

(SEQ ID NO: 12)
5'-TGACTCCATATGGAGTCACATCGGmCATCATTATTATCTTTGmUmGmAmAmC-3'

(SEQ ID NO: 4)
5'-GACTCGATATCGAGTCTTTCCGGmCATCATTATTATCTTTGmUmGmAmAmC-3'

(SEQ ID NO: 13)
5'-GAAAGACTCGCGAGTCTTTCCGGmCATCATTATTATCTTTGmUmGmAmAmC-3'

(SEQ ID NO: 14)
5'-TGACTCCATATGGAGTCACATTTTTCTCTGGmAmUmGmG-3'

(SEQ ID NO: 15)
5'-mUGCCGACTCGCGAGTCGGCATTTTCTCTGGmAmUmGmG-3'

(SEQ ID NO: 16)
5'-mGGCTGACTCCTGCAGGAGTCAGCCTTTTCTCTGGmAmUmGmG-3'

(SEQ ID NO: 17)
5'-mCAGCGACTCCCGGGAGTCGCTGTTTTCTCTGGmAmUmGmG-3', where "m" indicates the position of a modification.

In another aspect, the invention features a probe containing one of the following sequences:

(SEQ ID NO: 5)
5'-CGCCTGTGAACTTTATTGGCG-3'
or (SEQ ID NO: 18)
5'-ACCTGTTTACCGGGCATACAAACAGGT-3'.

In another aspect, the invention features a combination of primers and probes, where the primers contain the following sequences (SEQ ID NO: 3)
5' GACTCGATATCGAGTCTTTCCACmCGAAATACmCmGmCmCmA 3'

(SEQ ID NO: 4)
5' GACTCGATATCGAGTCTTTCCGGmCATCATTATTATCTTTGmUmGmAmAmC 3', and a detectable probe containing the following sequence:

(SEQ ID NO: 5)
5' CGCCTGTGAACTTTATTGGCG 3'.

In another aspect, the invention features a kit containing a nicking enzyme, dNTPs, a polymerase, a forward and a reverse primer selected from forward primers (SEQ ID NO: 6)
5'-TGACTCCATATGGAGTCACATCACmCGAAATACmCmGmCmCmA-3'

(SEQ ID NO: 3)
5'-GACTCGATATCGAGTCTTTCCACmCGAAATACmCmGmCmCmA-3'

(SEQ ID NO: 7)
5'-GAAAGACTCGCGAGTCTTTCCACmCGAAATACmCmGmCmCmA-3'

(SEQ ID NO: 8)
5'-TGACTCCATATGGAGTCACATATACTCATCTGTTmUmAmCmC-3'

(SEQ ID NO: 9)
5'-mUGCCGACTCGCGAGTCGGCAATACTCATCTGTTmUmAmCmC-3'

(SEQ ID NO: 10)
5'-mGGCTGACTCCTGCAGGAGTCAGCCATACTCATCTGTTmUmAmCmC-3'

(SEQ ID NO: 11)
5'-mCAGCGACTCCCGGGAGTCGCTGATACTCATCTGTTmUmAmCmC-3' and reverse primers:

(SEQ ID NO: 12)
5'-TGACTCCATATGGAGTCACATCGGmCATCATTATTATCTTTGmUmGmAmAmC-3'

(SEQ ID NO: 4)
5'-GACTCGATATCGAGTCTTTCCGGmCATCATTATTATCTTTGmUmGmAmAmC-3'

(SEQ ID NO: 13)
5'-GAAAGACTCGCGAGTCTTTCCGGmCATCATTATTATCTTTGmUmGmAmAmC-3'

(SEQ ID NO: 14)
5'-TGACTCCATATGGAGTCACATTTTTCTCTGGmAmUmGmG-3'

(SEQ ID NO: 15)
5'-mUGCCGACTCGCGAGTCGGCATTTTCTCTGGmAmUmGmG-3'

(SEQ ID NO: 16)
5'-mGGCTGACTCCTGCAGGAGTCAGCCTTTTCTCTGGmAmUmGmG-3'

(SEQ ID NO: 17)
5'-mCAGCGACTCCCGGGAGTCGCTGTTTTCTCTGGmAmUmGmG-3', where "m" indicates the position of a modification, and a probe containing one of the following sequences:

(SEQ ID NO: 5)
5'-CGCCTGTGAACTTTATTGGCG-3'
or (SEQ ID NO: 18)
5'-ACCTGTTTACCGGGCATACAAACAGGT-3'.

In another aspect, the invention features a kit containing a nicking enzyme, dNTPs, a polymerase, primers containing the following sequences

```
                                            (SEQ ID NO: 3)
5' GACTCGATATCGAGTCTTTCCACmCGAAATACmCmGmCmCmA 3'

(SEQ ID NO: 4)
5' GACTCGATATCGAGTCTTTCCGGmCATCATTATTATCTTTGmUm
GmAmAmC 3',
``` and a detectable probe containing the following sequence:

```
                                            (SEQ ID NO: 5)
        5' CGCCTGTGAACTTTATTGGCG 3'.
```

In various embodiments of the above aspects or any other aspect of the invention delineated herein, the sample contains a food product, environmental sample, biological sample or other material. In particular embodiments of the above aspects, the food product is intended for animal or human consumption. In other embodiments of the above aspects, the food product is pet food intended for consumption by a companion animal. In still other embodiments of the above aspects, the food product is or is derived from produce, poultry, fish, or beef. In still other embodiments of the above aspects, the environmental sample is a water, soil or sewage sample. In still other embodiments of the above aspects, the biological sample is feces or a blood sample. In still other embodiments of the above aspects, the sample is a culture medium. In still other embodiments of the above aspects, the Salmonella is selected from the group consisting of S typhi, S paratyphi-A, S schottmuelleri, S choleraesuis, S typhimurium and S enteritidis. In still other embodiments of the above aspects, the forward and reverse primers are selected from forward primers:

```
                                            (SEQ ID NO: 6)
5'-TGACTCCATATGGAGTCACATCACmCGAAATACmCmGmCmCmA-3'

(SEQ ID NO: 3)
5'-GACTCGATATCGAGTCTTTCCACmCGAAATACmCmGmCmCmA-3'

(SEQ ID NO: 7)
5'-GAAAGACTCGCGAGTCTTTCCACmCGAAATACmCmGmCmCmA-3'

(SEQ ID NO: 8)
5'-TGACTCCATATGGAGTCACATATACTCATCTGTTmUmAmCmC-3'

(SEQ ID NO: 9)
5'-mUGCCGACTCGCGAGTCGGCAATACTCATCTGTTmUmAmCmC-3'

(SEQ ID NO: 10)
5'-mGGCTGACTCCTGCAGGAGTCAGCCATACTCATCTGTTmUmAm
CmC-3'

(SEQ ID NO: 11)
5'-mCAGCGACTCCCGGGAGTCGCTGATACTCATCTGTTmUmAmCmC-3'
``` and reverse primers:

```
                                            (SEQ ID NO: 12)
5'-TGACTCCATATGGAGTCACATCGGmCATCATTATTATCTTTGmUmGm
AmAmC-3'

(SEQ ID NO: 4)
5'-GACTCGATATCGAGTCTTTCCGGmCATCATTATTATCTTTGmUmGm
AmAmC-3'
```

```
                                            (SEQ ID NO: 13)
5'-GAAAGACTCGCGAGTCTTTCCGGmCATCATTATTATCTTTGmUmGm
AmAmC-3'

(SEQ ID NO: 14)
5'-TGACTCCATATGGAGTCACATTTTTCTCTGGmAmUmGmG-3'

(SEQ ID NO: 15)
5'-mUGCCGACTCGCGAGTCGGCATTTTCTCTGGmAmUmGmG-3'

(SEQ ID NO: 16)
5'-mGGCTGACTCCTGCAGGAGTCAGCCTTTTCTCTGGmAmUmGmG-3'

(SEQ ID NO: 17)
5'-mCAGCGACTCCCGGGAGTCGCTGTTTTCTCTGGmAmUmGmG-3',
``` where "m" indicates the position of a modification. In still other embodiments of the above aspects, the amplicon is detected with a probe containing one of the following sequences:

```
                                            (SEQ ID NO: 5)
        5'-CGCCTGTGAACTTTATTGGCG-3'
        or
                                            (SEQ ID NO: 18)
        5'-ACCTGTTTACCGGGCATACAAACAGGT-3'.
```

In still other embodiments of the above aspects, the probe contains a fluorescent moiety and a quencher. In still other embodiments of the above aspects, the fluorescent moiety is CalRed$_{610nm}$ and the quencher is Black Hole Quencher2 (BHQ2). In still other embodiments of the above aspects, the forward and reverse primers comprise the following sequences, respectively:

```
                                            (SEQ ID NO: 3)
5' GACTCGATATCGAGTCTTTCCACmCGAAATACmCmGmCmCmA 3'

(SEQ ID NO: 4)
5' GACTCGATATCGAGTCTTTCCGGmCATCATTATTATCTTTGmUmGm
AmAmC 3'
``` and a probe contains the following sequence:

```
                                            (SEQ ID NO: 5)
        5' CGCCTGTGAACTTTATTGGCG 3'.
```

In still other embodiments of the above aspects, the nicking enzyme is any one or more of N.Bst9I, N.BstSEI, Nb.BbvCI (NEB), Nb.Bpu10I(Fermantas), Nb.BsmI(NEB), Nb.BsrDI (NEB), Nb.BtsI(NEB), Nt.AlwI(NEB), Nt.BbvCI(NEB), Nt.Bpu10I(Fermentas), Nt.BsmAI, Nt.BspD6I, Nt.BspQI (NEB), Nt.BstNBI(NEB), and Nt.CviPII(NEB). In still other embodiments of the above aspects, the polymerase is Bst DNA polymerase I or Gst DNA polymerase I. In still other embodiments of the above aspects, the method is used periodically to monitor a site selected from the group consisting of a field, crop, herd, food processing facility, and food handling facility for the presence of Salmonella. In still other embodiments of the above aspects, the monitoring is conducted about every 1, 3, 6, 9, or 12 months. In still other embodiments of the above aspects, the modification is selected from the group consisting of 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-CH$_2$—O-2'-bridge, 4'-(CH$_2$)$_2$—O-2'-bridge, and 2'-O—(N-methylcarbamate).

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "amplicon" is meant a polynucleotide generated during the amplification of a polynucleotide of interest. In one example, the amplicon comprises at least a portion of a *Salmonella* invA polynucleotide.

By "base substitution" is meant a substituent of a nucleobase polymer that does not cause significant disruption of the hybridization between complementary nucleotide strands.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "complementary" or "complementarity" is meant that a nucleic acid can form hydrogen bond(s) with another nucleic acid sequence by either traditional Watson-Crick or Hoogsteen base pairing. Complementary base pairing includes not only G-C and A-T base pairing, but also includes base pairing involving universal bases, such as inosine. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

"Detect" refers to identifying the presence, absence or amount of the analyte to be detected. In one embodiment, the analyte is a *Salmonella* polynucleotide. In a working example, an assay of the invention detects the presence of *Salmonella* in a matrix of the invention.

By "detectable probe" is meant a composition that when linked to a moiety of interest renders the latter detectable, via spectroscopic, photochemical, biochemical, immunochemical, or chemical means. For example, useful detectable moieties include radioactive isotopes, magnetic beads, metallic beads, colloidal particles, fluorescent dyes, electron-dense reagents, enzymes (for example, as commonly used in an ELISA), biotin, digoxigenin, or haptens. In one embodiment, a detectable probe is a molecular beacon.

By "food product" is meant any material intended for animal or human consumption.

By "hybridize" is meant to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Hybridization occurs by hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA, RNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "nicking agent" is meant a chemical entity capable of recognizing and binding to a specific structure in double stranded nucleic acid molecules and breaking a phosphodiester bond between adjoining nucleotides on a single strand upon binding to its recognized specific structure, thereby creating a free 3'-hydroxyl group on the terminal nucleotide preceding the nick site. In preferred embodiments, the 3' end can be extended by an exonuclease deficient polymerase. Exemplary nicking agents include nicking enzymes, RNAzymes, DNAzymes, and transition metal chelators.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2' modified nucleotides (e.g., 2'-O-methyl, 2'-F nucleotides).

By "periodic" is meant at regular intervals. Periodic monitoring includes, for example, a schedule of tests that are administered daily, bi-weekly, bi-monthly, monthly, bi-annually, or annually.

By "polymerase-arresting molecule" is meant a moiety associated with a polynucleotide template/primer that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase that matches incoming monomers to their binding partners on a template polynucleotide.

By "reference" is meant a standard or control condition.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "specific product" is meant a polynucleotide product resulting from the hybridization of primer oligonucleotides to a complementary target sequence and subsequent polymerase mediated extension of the target sequence.

By "specifically binds" is meant an oligonucleotide probe of the invention that binds a polynucleotide of the invention, but which does not substantially recognize and bind other polynucleotides in a sample, for example, a biological sample.

By "substantially isothermal condition" is meant at a single temperature or within a narrow range of temperatures that does not vary significantly.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 provides the sequence of the *Salmonella* invA gene (SEQ ID NO: 22). Highlighted in gray are the target sequence regions used for design of isothermal detection assays. The target sequence region of a commercially available *Salmonella* invA assay used herein as a reference assay is shown in bold, underlined letters.

FIG. 2 provides exemplary primer sequences for amplifying an "invA" target sequence region I, and an exemplary probe sequence for detecting the amplicons (SEQ ID NOS 6, 3, 7, 12, 4, 13, and 5, respectively, in order of appearance).

FIG. 3 provides exemplary primer sequences for amplifying an "invA" target sequence region II, and an exemplary probe sequence for detecting the amplicons (SEQ ID NOS 8-11 and 14-18, respectively, in order of appearance).

FIG. 4 provides isothermal amplification plots showing an analytical limit of detection (ALOD) for *Salmonella enterica* "invA" Region I DNAble assay. Results depicted in FIGS. 4-6 were obtained using the primers and probes delineated in FIG. 2 with an asterisk.

FIG. 5 provides isothermal amplification plots showing the Biological Limit of Detection (BLOD) of *Salmonella enterica* "invA" Region I analyzed using a DNAble Assay.

DETAILED DESCRIPTION OF THE INVENTION

Figure 6A:
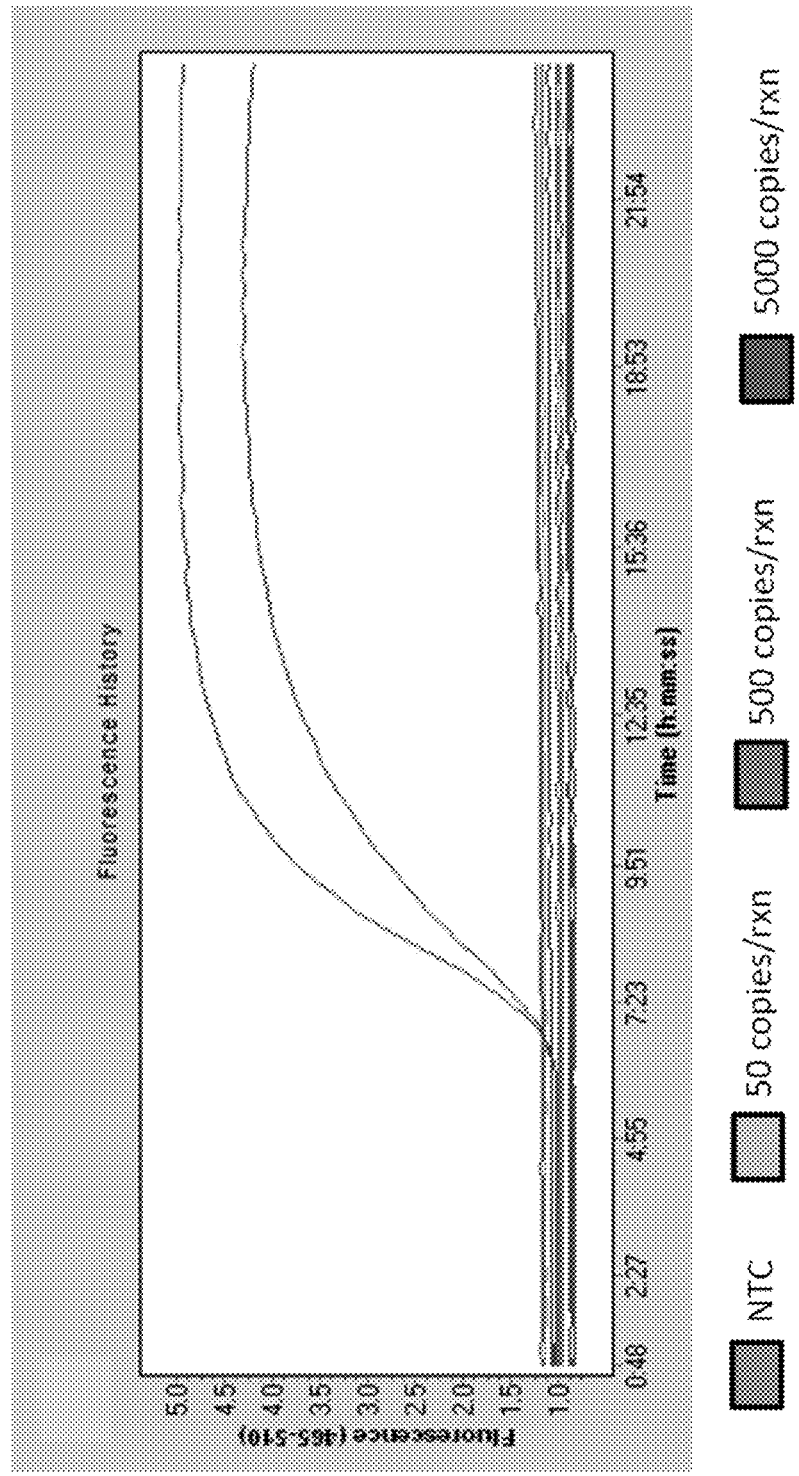
FIG. 6, comprising FIGS. 6A and 6B, provides a comparison of isothermal amplification plots obtained using a DNAble assay of the invention (shown in FIG. 6B) and a commercially available NEAR assay targeting invA (shown in FIG. 6A).

As described below, the present invention features rapid and accurate methods for detecting *Salmonella* in a sample (e.g., in a food product, environmental sample, biological sample or other material).

The invention is based, at least in part, on the discovery that *Salmonella* can be detected by assaying food, environmental (e.g., water, soil, sewage or other waste product), biological sample (e.g., feces) or other samples using an isothermal nicking amplification reaction.

Salmonella

*Salmonella* species are Gram-negative, flagellated facultatively anaerobic bacilli. There are over 1800 known serovars which current classification considers to be separate species. The most common human and animal pathogens include, but are not limited to, *S typhi*, *S paratyphi*-A, *S schottmuelleri*, *S choleraesuis*, *S typhimurium* and *S enteritidis*. The most common animal reservoirs are chickens, turkeys, pigs, and cows; dozens of other domestic and wild animals also harbor these organisms.

*Salmonellosis* ranges clinically from the common *Salmonella* gastroenteritis (diarrhea, abdominal cramps, and fever) to enteric fevers (including typhoid fever) which are life-threatening febrile systemic illness requiring prompt antibiotic therapy. Focal infections and an asymptomatic carrier state occur. The most common form of *salmonellosis* is a self-limited, uncomplicated gastroenteritis.

Pathogenic salmonellae ingested in food survive passage through the gastric acid barrier and invade the mucosa of the small and large intestine and produce toxins. Invasion of epithelial cells stimulates the release of proinflammatory cytokines which induce an inflammatory reaction. The acute inflammatory response causes diarrhea and may lead to ulceration and destruction of the mucosa. The bacteria can disseminate from the intestines to cause systemic disease.

Nucleic Acid Amplification Methods

Nucleic acid amplification technologies have provided a means of understanding complex biological processes, detection, identification, and quantification of *Salmonella*. The present invention provides for the detection of *Salmonella* in a sample by amplifying the DNA in an isothermal nicking amplification reaction and is designed to detect all serovars of *Salmonella*.

The polymerase chain reaction (PCR) is a common thermal cycling dependent nucleic acid amplification technology used to amplify DNA consisting of cycles of repeated heating and cooling of the reaction for DNA melting and enzymatic replication of the DNA using a DNA polymerase. Real-Time quantitative PCR (qPCR) is a technique used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, typically based on the logarithmic portion of the standard reaction amplification curves. These values are used to interpolate the quantity of the unknowns based on where their amplification curves compared to the standard control quantities.

In addition to PCR, non-thermal cycling dependent amplification systems or isothermal nucleic acid amplification technologies exist including, without limitation: Nicking Amplification Reaction, Rolling Circle Amplification (RCA), Helicase-Dependent Amplification (HDA), Loop-Mediated Amplification (LAMP), Strand Displacement Amplification (SDA), Transcription-Mediated Amplification (TMA), Self-Sustained Sequence Replication (3SR), Nucleic Acid Sequence Based Amplification (NASBA), Single Primer Isothermal Amplification (SPIA), Q-β Replicase System, and Recombinase Polymerase Amplification (RPA).

Isothermal nicking amplification reactions have similarities to PCR thermocycling. Like PCR, nicking amplification reactions employ oligonucleotide sequences which are complementary to a target sequences referred to as primers. In addition, nicking amplification reactions of target sequences results in a logarithmic increase in the target sequence, just as it does in standard PCR. Unlike standard PCR, the nicking amplification reactions progress isothermally. In standard PCR, the temperature is increased to allow the two strands of DNA to separate. In nicking amplification reactions, the target nucleic acid sequence is nicked at specific nicking sites present in a test sample. The polymerase infiltrates the nick site and begins complementary strand synthesis of the nicked target nucleotide sequence (the added exogenous DNA) along with displacement of the existing complimentary DNA strand. The strand displacement replication process obviates the need for increased temperature. At this point, primer molecules anneal to the displaced complementary sequence from the added exogenous DNA. The polymerase now extends from the 3' end of the template, creating a complementary strand to the previously displaced strand. The second oligonucleotide primer then anneals to the newly synthesized complementary strand and extends making a duplex of DNA which includes the nicking enzyme recognition sequence. This strand is then liable to be nicked with subsequent strand displacement extension by the polymerase, which leads to the production of a duplex of DNA which has nick sites on either side of the original target DNA. Once this is synthesized, the molecule continues to be amplified exponentially through replication of the displaced strands with new template molecules. In addition, amplification also proceeds linearly from each product molecule through the repeated action of the nick translation synthesis at the template introduced nick sites. The result is a very rapid increase in target signal amplification; much more rapid than PCR thermocycling, with amplification results in less than ten minutes.

Nicking Amplification Assays

The invention provides for the detection of *Salmonella* target nucleic acid molecules amplified in an isothermal nicking amplification assay. Such assays are known in the art and described herein. See, for example, US Patent Application Publication 2009/0081670, PCT Application 2009/012246, and U.S. Pat. Nos. 7,112,423 and 7,282,328, each of which is incorporated herein in its entirety. Polymerases useful in the methods described herein are capable of catalyzing the incorporation of nucleotides to extend a 3' hydroxyl terminus of an oligonucleotide (e.g., a primer) bound to a target nucleic acid molecule. Such polymerases include those that are thermophilic and/or those capable of strand displacement. In one embodiment, a polymerase lacks or has reduced 5'-3' exonuclease activity and/or strand displacement activity. DNA polymerases useful in methods involving primers having 2'-modified nucleotides at the 3' end include derivatives and variants of the DNA polymerase I isolated from *Bacillus stearothermophilus*, also taxonomically re-classified as *Geobacillus stearothermophilus*, and closely related thermophilic bacteria, which lack a 5'-3' exonuclease activity and have strand-displacement activity. Exemplary polymerases include, but are not limited to the fragments of Bst DNA polymerase I and Gst DNA polymerase I.

A nicking enzyme binds double-stranded DNA and cleaves one strand of a double-stranded duplex. In the methods of the invention, the nicking enzyme cleaves the top stand (the strand comprising the 5'-3' sequence of the nicking agent recognition site). In a particular embodiment of the invention disclosed herein, the nicking enzyme cleaves the top strand only and 3' downstream of the recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking enzymes include, but are not limited to, N.Bst9I, N.BstSEI, Nb.BbvCI(NEB), Nb.Bpu10I(Fermantas), Nb.BsmI(NEB), Nb.BsrDI(NEB), Nb.BtsI(NEB), Nt.AlwI(NEB), Nt.BbvCI(NEB), Nt.Bpu10I(Fermentas), Nt.BsmAI, Nt.BspD6I, Nt.BspQI(NEB), Nt.BstNBI(NEB) and Nt.CviPII(NEB). Sequences of nicking enzyme recognition sites are provided at Table 1.

TABLE 1

Nicking enzyme recognition sequences

N.Bst9I          5'-GAGTCNNNNN↓NN-3' (SEQ ID NO: 19)
                    ||||||||||  ||
                 3'-CTCAGNNNNN·NN-5'

N.BstSEI         5'-GAGTCNNNNN↓NN-3' (SEQ ID NO: 19)
                    ||||||||||  ||
                 3'-CTCAGNNNNN·NN-5'

Nb.BbvCI(NEB)    5'-CCTCA·GC-3'
                    ||||| |
                 3'-GGAGT↑CG-5'

Nb.Bpu10I        5'-CCTNA·GC-3'
(Fermantas)         ||||| ||
                 3'-GGANT↑CG-5'

Nb.BsmI(NEB)     5'-GAATG·CN-3'
                    ||||| ||
                 3'-CTTAC↑GN-5'

Nb.BsrDI(NEB)    5'-GCAATG·NN-3'
                    |||||| ||
                 3'-CGTTAC↑NN-5'

Nb.BtsI(NEB)     5'-GCAGTG·NN-3'
                    |||||| ||
                 3'-CGTCAC↑NN-5'

Nt.AlwI(NEB)     5'-GGATCNNNN↓N-3' (SEQ ID NO: 20)
                    |||||||||  |
                 3'-CCTAGNNNN·N-5'

Nt.BbvCI(NEB)    5'-CC↓TCAGC-3'
                    || |||||
                 3'-GG·AGTCG-5'

Nt.Bpu10I        5'-CC↓TNAGC-3'
(Fermentas)         || |||||
                 3'-GG·ANTCG-5'

Nt.BsmAI         5'-GTCTCN↓N-3'
                    |||||| |
                 3'-CAGAGN·N-5'

Nt.BspD6I        5'-GAGTCNNNN↓N-3' (SEQ ID NO: 21)
                    |||||||||  |
                 3'-CTCAGNNNN·N-5'

TABLE 1-continued

Nicking enzyme recognition sequences

Nt.BspQI(NEB)    5'-GCTCTTCN↓-3'
                    ||||||||
                 3'-CGAGAAGN-5'

Nt.BstNBI(NEB)   5'-GAGTCNNNN↓N-3' (SEQ ID NO: 21)
                    |||||||||  |
                 3'-CTCAGNNNN·N-5'

Nt.CviPII(NEB)   5'-↓CCD-3'
                    |||
                 3'-GGH-5'

Nicking enzymes also include engineered nicking enzymes created by modifying the cleavage activity of restriction endonucleases (NEB expressions July 2006, vol 1.2). When restriction endonucleases bind to their recognition sequences in DNA, two catalytic sites within each enzyme for hydrolyzing each strand drive two independent hydrolytic reactions which proceed in parallel. Altered restriction enzymes can be engineered that hydrolyze only one strand of the duplex, to produce DNA molecules that are "nicked" (3'-hydroxyl, 5'-phosphate), rather than cleaved. Nicking enzymes may also include modified CRISPR/Cas proteins, Transcription activator-like effector nucleases (TALENs), and Zinc-finger nucleases having nickase activity.

A nicking amplification reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The reaction further comprises certain salts and buffers that provide for the activity of the nicking enzyme and polymerase.

This invention provides methods of monitoring a nicking amplification reaction in real time, utilizing the amplification strategy as described above. In one embodiment, quantitative nucleic acid amplification utilizes target nucleic acids amplification alongside a control amplification of known quantity. The amount of target nucleic acid can be calculated as an absolute quantification or a relative quantification (semi-quantitative) based on the source of the control (exogenous or endogenous control).

Quantification of the unknown nucleotide sequence can be achieved either through comparison of logarithmic threshold amplification of the unknown to a series of known target sequences in either a separate set of reactions or in the same reaction; or as an internal endogenous or exogenous co-amplification product which produces a threshold value, indicative of either a positive result (if the unknown exceeds the threshold) or negative result (if the unknown does not exceed the threshold).

3' Recognition Region

The invention provides a primer having a 3' recognition sequence whose primer-target formation is stable and has the potential to enhance *Salmonella* nucleic acid amplification reaction performance. The 3' recognition region specifically binds to the *Salmonella* nucleic acid molecule, for example a complementary sequence of the *Salmonella* nucleic acid molecule.

In particular, a primer of the invention having a 3' recognition sequence is useful in nicking amplification assays. Additionally, the *Salmonella* target specific 3' recognition region comprises one or more 2' modified nucleotides (e.g., 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-CH$_2$—O-2'-bridge, 4'-(CH$_2$)$_2$—O-2'-bridge, and 2'-O—(N-methylcarbamate)). Without being bound to theory, it is hypothesized that incorporating one or more 2' modified nucleotides in the recognition regions reduces or eliminates intermolecular and/or intramolecular interactions of primers/templates (e.g., primer-dimer formation), and, thereby, reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the *Salmonella* target specific recognition region are contiguous (e.g., a block of modified nucleotides). In some embodiments, the block of 2' modified nucleotides is positioned at the 3' end of the target specific recognition region. In other embodiments, the block of 2' modified nucleotides is positioned at the 5' end of the *Salmonella* target specific recognition region. When the block of 2' modified nucleotides is positioned at the 5' end of the target specific recognition region, the 2' modified nucleotides may be separated from the nick site by one or more non-modified nucleotides (e.g., 2, 3, 4, 5 or more 2' unmodified nucleotides). Applicants have found that positioning of one or more 2' modified nucleotides or of a block of 2' modified nucleotides alters the kinetics of amplification. When the one or more 2' modified nucleotides or block of 2' modified nucleotides are positioned at or near the 5' end of the recognition region or proximal to the nick site, real-time amplification reactions showed decreased time to detection. Additionally, the signal curve is contracted and the slope of the curve shifted.

In a related embodiment, ratios of a primer having one or more 2' modified nucleotides can be used to alter the time-to-detection and/or the efficiency of the reaction for the 'tuning' of reactions, resulting in a predictable control over reaction kinetics. Increasing the ratio of primer having one or more 2' modified nucleotides at the 3' end of the recognition sequence to primer having one or more 2' modified nucleotides at the 5' end of the recognition sequence contracted the signal curve and shifted the slope of the curve. It is advantageous to be able to "tune" a reaction providing a means to manipulate both the time-to-detection as well as the efficiency of the reaction. Relative quantification using an internal control requires that two important conditions be met. First, it is beneficial to be able to modify a reaction's time-to-detection creating a non-competitive reaction condition. Thus, by affecting the control reaction to be detectable at a later time-point (relative to the target of interest) the control reaction does not out-compete the specific target of interest even when the target of interest is in low initial abundance. Second, to ensure a true relative abundance calculation, it is required that the control and specific target reactions have matched efficiencies. By controlling the efficiency of each reaction using a "tuning" condition enables reactions to be matched allowing for satisfactory relative quantification calculations. Tuning the reactions can be used to match efficiencies of target nucleic acid amplification and reference nucleic amplification (e.g., internal standard) in quantitative PCR (qPCR). Additionally, amplification curves of the target nucleic acid and the internal standard may be altered so time of detection of their amplification products are separated, while providing the same efficiency for target nucleic acid amplification and internal standard amplification. Through the use of specific combinations and ratios of oligonucleotide structures within a reaction it is possible to create conditions which enable tuned reaction performance.

Target Nucleic Acid Molecules

Methods and compositions of the invention are useful for the amplification and/or identification of a *Salmonella* nucleic acid molecule in a test sample. The target sequences is amplified from virtually any sample that comprises a *Salmonella* nucleic acid molecule.

Exemplary test samples include environmental samples, agricultural products or other foodstuffs, and their extracts, body fluids (e.g. blood, serum, plasma, feces, or gastric fluid), tissue extracts, and culture media (e.g., a liquid in which a cell, such as a pathogen cell, has been grown). If desired, the sample is purified prior to inclusion in a nicking amplification reaction using any standard method typically used for isolating a nucleic acid molecule from a biological sample.

In one embodiment, primers amplify a target nucleic acid of a pathogen to detect the presence of *Salmonella* in a sample. Methods of the invention provide for the detection of 50 copies per reaction are detected *Salmonella* in a sample.

Applications

Target nucleic acid amplification using primers of the invention have characteristics useful for rapid detection of *Salmonella* nucleic acid molecules. Compositions and methods of the invention are particularly useful for the detection of contaminated food products, where a rapid answer is desired (e.g., detectable amplification in under 15, 10, 9, 8, 7, 6, 5 minutes or less).

In particular embodiments, the invention provides for the use of a *Salmonella* nicking amplification reaction assay in the field, in containers for transport, in warehouses, grain elevators, food processing facilities, grocery stores, restaurants, kitchens, or any other venue where food is handled, stored, or prepared for human or animal consumption. In other embodiments, the sample is an environmental sample, including but not limited to, water, soil, waste product (e.g., feces), boot swabs, or sewage. In particular embodiments, the invention is useful for assaying a poultry and birds (e.g., chicken, turkey, geese, ducks, wild flocks), for facilities where poultry is processed (e.g., slaughter house, coops) and from poultry derived food stuffs, including eggs and egg products (e.g., egg whites). In other embodiments, the invention provides for the use of nicking amplification reaction assays in field work, where access to thermocycling equipment is unavailable or would be prohibitively expensive. In still other embodiments, the invention provides for the use of nicking amplification reaction assays in a setting where rapid quantitative answers are desired.

Detectable Oligonucleotide Probes

The present invention provides for the quantitative detection of target nucleic acid molecules or amplicons thereof in a nicking amplification reaction using non-amplifiable detectable polynucleotide probes comprising at least one polymerase-arresting molecule (e.g., nucleotide modification or other moiety (e.g., quencher, fluorescent moiety) that renders the oligonucleotide capable of binding a target nucleic acid molecule, but incapable of supporting template extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, other spacer moiety, O-2-Me bases). These constructs thus prevent or reduce illegitimate amplification of the probe during the course of a nicking amplification reaction. This distinguishes them from conventional detection probes, which must be added at the end of the nicking amplification reaction to prevent their amplification.

Conventional detection probes have proven impractical for quantitating a nicking amplification reaction in real time. If conventional detection probes are incorporated into the nicking amplification reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise at least one polymerase-arresting molecule. A polymerase-arresting molecule of the invention includes, but is not limited to, a nucleotide modification or other moiety that blocks template extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, a detectable oligonucleotide probe comprises one or more modified nucleotide bases having enhanced binding affinity to a complementary nucleotide. Examples of modified bases include, but are not limited to 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be quantitated simultaneously. The present invention encompasses the use of such fluorophores in conjunction with the detectable oligonucleotide probes described herein.

Kits

The invention also provides kits for the detection of a target *Salmonella* nucleic acid molecule. Such kits are useful for the detection or quantitation of a target *Salmonella* nucleic acid in a sample (e.g., food product, environmental sample, biological sample or other material). Kits of the present invention may comprise, for example, one or more polymerases, forward and reverse primers, and one or more nicking enzymes, and a detectable probe as described herein. Where one target is to be amplified, one or two nicking enzymes may be included in the kit.

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primers capable of binding to and amplifying a reference sequence that can be used as a positive control. In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the primers. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the primers are either lyophilized, freeze dried, or in buffer, in a different container. In some embodiments, the polymerase, nicking enzymes, and the primers are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Test Kit for Qualitative Detection of DNA from *Salmonella*

Rapid, point of need detection of *Salmonella* is required to effect interventions to prevent its spread. A test kit was generated for qualitative detection of DNA from *Salmonella*. The sequence of the invA target gene is provided in FIG. 1. The detection assay is based on an isothermal nucleic acid amplification method. Test samples were prepared from simulated pet food or enriched culture. 1 mL of enriched sample was added to a microcentrifuge tube and centrifuged at 10,000×G for 5 minutes. The supernatant was discarded and the pellet was suspended in 100 µL of a buffer comprising Tris-Hcl, Magnesium Sulfate, Sodium Sulfate, Ammonium Sulfate, and Triton X 100. The sample and buffer are heated to 95° C. for 5 minutes then centrifuged to pellet the debris. The supernatant was diluted 1:10 in the buffer, and 5 µl of crude prep was diluted in 50 µl buffer. The amplification reaction was run at 56° C. The amplification reaction contains excess of forward primer (e.g., 600, 800 nM), 100-200 nM reverse primer, 300-400 nM probe, 250-300 nM dNTPs, 10-20 Units a Bst DNA polymerase I, and 7-8 units of nicking enzyme Nt.BstNBI(NEB), dNTPs. The sequences of primers and probes is provided at FIGS. 2 and 3.

The amplification and detection reactions displayed a high signal to noise ratio, early onset of exponential amplification, steep amplification slope, rapid time to detection, and low signal variance among replicated assay reactions. All target control samples showed robust signal. The assay was further tested and detected a list of over 100 *Salmonella* serotypes. These results indicate that the provides compositions and methods for the rapid and sensitive detection of *Salmonella*.

Example 2

Analytical Limit of Detection (ALOD) of *Salmonella*

FIG. 4 shows isothermal amplification plots of a target genomic DNA dilution series of DNAble assay reactions targeting region 1 of the "invA" gene carried out on a LC480 thermocycler from Roche Diagnostics Inc. The target-specific probe signal was detected in the 533-610 nm fluorescence channel. All reactions were set-up in 50 µl volume using 800 nmol of the forward primer, 200 nmol of the reverse primer and 400 nmol of the molecular beacon probe under reaction conditions described herein above. In sets of three technical replicates for each copy number, various amounts of purified *Salmonella enterica* genomic DNA ranging from 0 copies per reaction (no target control reactions, blue amplification plots), 50 copies per reaction (yellow amplification plots), 500 copies per reaction (black amplification plots), 5000 copies per reaction (purple amplification plots), 50,000 copies per reaction (yellow amplification plots) and 500,000 copies per reaction (red amplification plots) were added to the reaction. Reliable detection of the region I "invA" target is demonstrated down to 50 copies per 50 µl reaction.

Example 3

Biological Limit of Detection (BLOD) of *Salmonella*

FIG. 5 shows isothermal amplification plots of DNAble assay reactions targeting region I of the "invA" gene carried out on a LC480 thermocycler from Roche Diagnostics Inc. A target-specific probe signal was detected in the 533-610 nm fluorescence channel. All reactions were set-up in 50 µl volume using 800 nmol of the forward primer with the optimal 5'-tail combination, 200 nmol of the reverse primer with optimal 5'-tail combination and 400 nmol of the molecular beacon probe under standard reaction conditions described herein above. In sets of three technical replicates, crude samples containing *Salmonella enterica* genomic DNA extracted from bacterial cultures inoculated with counts of live *Salmonella* cells equivalent to colony forming units (CFU) ranging from 0 CFU per reaction (NTC, i.e. no target control reactions, orange amplification plots), $10^4$ CFU per reaction (black amplification plots), $10^5$ CFU per reaction (turquoise amplification plots), $10^6$ CFU (brown amplification plots) and $10^7$ CFU per reaction (yellow amplification plots) were added to the reaction. Reliable detection of the region I "invA" target is demonstrated down to $10^4$ CFU per 50 µl reaction.

Example 4

*Salmonella* Assay Comparison

Figure 6B:
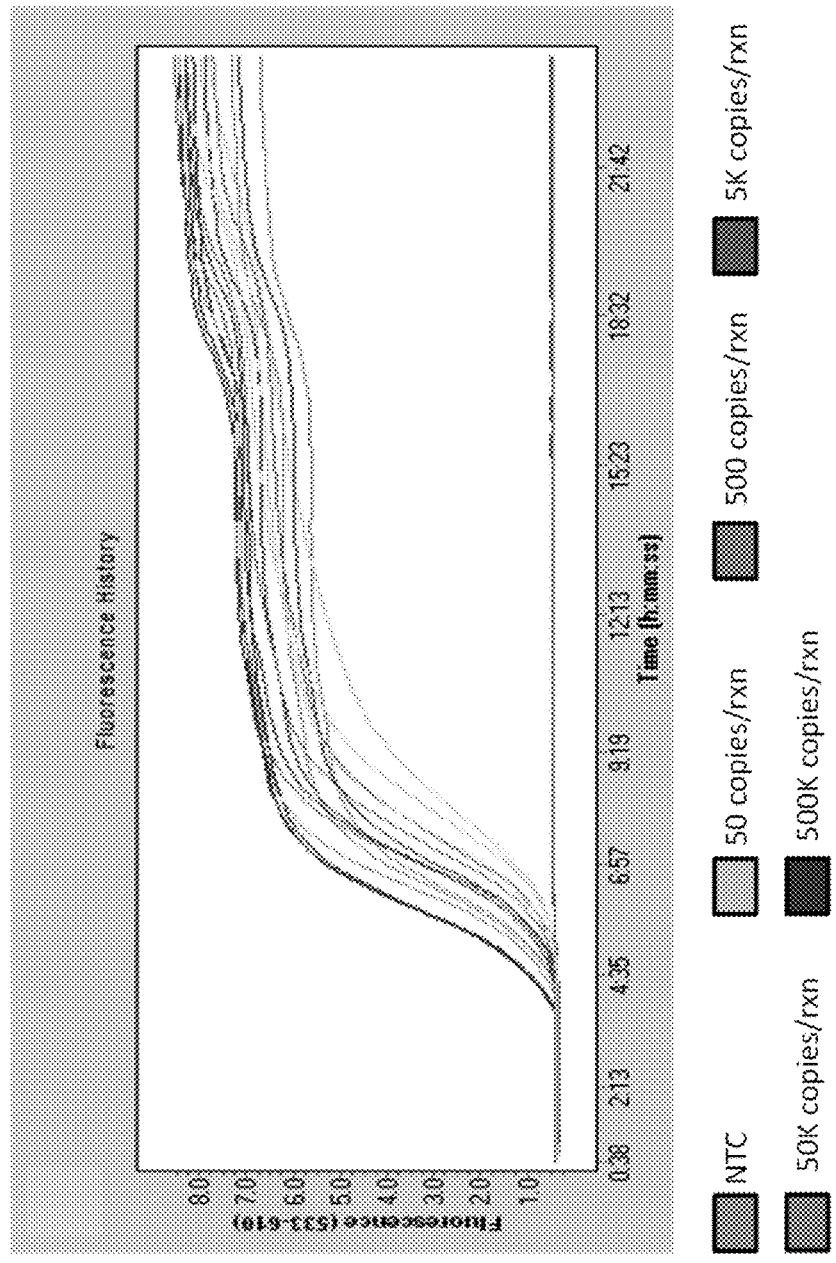

FIG. 6 shows amplification plots of a commercially available isothermal amplification assay based on the NEAR technology (FIG. 6A) and amplification plots carried out using primers and probes (FIG. 2) targeting region 1 of the "invA" gene (FIG. 6B). All reactions were carried out on a LC480 thermocycler from Roche Diagnostics Inc. The target-specific probe signal was detected in the 533-610 nm fluorescence channel. Reactions of both assays were set-up in 50 µl volume as described elsewhere. In sets of two (FIG. 6A) and three (FIG. 6B) technical replicates for each gDNA copy number, various amounts of purified *Salmonella enterica* genomic DNA ranging from 0 copies per reaction (NTC, i.e. no target control reactions, blue amplification plots), 50 copies per reaction (yellow amplification plots), 500 copies per reaction (black amplification plots), 5000 copies per reaction (purple amplification plots), 50,000 copies per reaction (yellow amplification n plots) and 500,000 copies per reaction (red amplification plots) were added to the reaction. The commercial NEAR-based assay failed to detect the "invA" target sequence at gDNA copy numbers <5000/reaction.

Example 5

Specificity of the *Salmonella* Assay

Using the reaction conditions described herein above, the *Salmonella* strains delineated below were tested with the DNAble 3.0 *Salmonella* assay. The assay successfully detected all of the *Salmonella* strains identified in the "Inclusivity list." The assay did not cross-react with the bacteria listed on the "Exclusivity list."

| Exclusivity List: | |
| --- | --- |
| Strain name | DNAble results |
| *Shigella flexneri** | Neg |
| *Yersinia enterocolitica** | Neg |
| *Vibrio cholera** | Neg |
| *Klebsiella pneumoniae** | Neg |
| *Bacillus cereus** | Neg |
| *Clostridium difficile** | Neg |
| *L. monocytogenes* | Neg |
| *L. innocua* | Neg |
| *S. boydii* | Neg |
| *Y. enterocolitica* | Neg |
| *S. dysenteriae* | Neg |

Exclusivity List:

| Strain name | DNAble results |
|---|---|
| C. jejuni | Neg |
| C. jejuni | Neg |
| C. coli | Neg |
| C. coli | Neg |
| P. vulgaris | Neg |
| C. sakazakii | Neg |
| Staphylococcus aureus | Neg |
| Serratia sp. | Neg |
| E. cloacae | Neg |
| M. morganii | Neg |
| E. cloacae | Neg |
| L. monocytogenes | Neg |
| E. aerogenes | Neg |
| C. fruendii | Neg |

Inclusivity List:

| Salmonella strain (Genus and species) | Serotype | DNAble results |
|---|---|---|
| Salmonella enterica | 1,4,(5),12:i:- | Pos |
| Salmonella enterica | Arizonae | Pos |
| Salmonella enterica | Arizonae | Pos |
| Salmonella bongori* | | Pos |
| Salmonella bongori* | | Pos |
| Salmonella enterica | Choleraesuis | Pos |
| Salmonella enterica | Diarizonae | Pos |
| Salmonella enterica | Dublin** | Pos |
| Salmonella enterica | Dublin** | Pos |
| Salmonella enterica | Enteritidis** | Pos |
| Salmonella enterica | Enteritidis** | Pos |
| Salmonella enterica | Gallinarum | Pos |
| Salmonella enterica | Hadar | Pos |
| Salmonella enterica | Heidelberg** | Pos |
| Salmonella enterica | heidelberg** | Pos |
| Salmonella enterica | heidelberg** | Pos |
| Salmonella enterica | infantis** | Pos |
| Salmonella enterica | Javiana | Pos |
| Salmonella enterica | Kentucky | Pos |
| Salmonella enterica | Kentucky** | Pos |
| Salmonella enterica | Newport | Pos |
| Salmonella enterica | Newport** | Pos |
| Salmonella enterica | newport** | Pos |
| Salmonella enterica | ParatyphiA | Pos |
| Salmonella enterica | ParatyphiB | Pos |
| Salmonella enterica | ParatyphiC | Pos |
| Salmonella enterica | Pullorum | Pos |
| Salmonella enterica | Pullorum** | Pos |
| Salmonella bongori* | | Pos |
| Salmonella enterica | S. enterica enterica* | Pos |
| Salmonella enterica | S. enterica enterica | Pos |
| Salmonella enterica | S. Enteritidis** | Pos |
| Salmonella enterica | S. typhimurium* | Pos |
| Salmonella enterica | SaintPaul | Pos |
| Salmonella enterica | Schwarzengrund | Pos |
| Salmonella enterica | Typhi** | Pos |
| Salmonella enterica | Typhimurium | Pos |
| Salmonella enterica | Typhimurium** | Pos |
| Salmonella enterica | Meleagridis** | Pos |
| Salmonella enterica | Orion va. 15+, 34+** | Pos |
| Salmonella enterica | Tennessee** | Pos |
| Salmonella enterica | Hartford** | Pos |
| Salmonella enterica | Virchow** | Pos |
| Salmonella enterica | Uganda** | Pos |
| Salmonella enterica | Dessau** | Pos |
| Salmonella enterica | T. Copenhagen** | Pos |
| Salmonella enterica | Senftenberg** | Pos |
| Salmonella enterica | Give** | Pos |
| Salmonella enterica | Cerro** | Pos |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A primer selected from the group consisting of a forward primer having the nucleic acid sequence:

(SEQ ID NO: 3)
5'-GACTCGATATCGAGTCTTTCCAC[mC]GAAATAC[mC][mG][mC][mC][mA]-3' and a reverse primer having the nucleic acid sequence:

(SEQ ID NO: 4)
5'-GACTCGATATCGAGTCTTTCCGG[mC]ATCATTATTATCTTTG[mU][mG][mA][mA][mC]-3', wherein "m" preceding a nucleotide indicates the position of a 2' modification on the nucleotide.

2. A pair of primers comprising a forward primer having the nucleic acid sequence:

(SEQ ID NO: 3)
5'-GACTCGATATCGAGTCTTTCCAC[mC]GAAATAC[mC][mG][mC][mC][mA]-3' and a reverse primer having the nucleic acid sequence:

(SEQ ID NO: 4)
5'-GACTCGATATCGAGTCTTTCCGG[mC]ATCATTATTATCTTTG[mU][mG][mA][mA][mC]-3', wherein "m" preceding a nucleotide indicates the position of a 2' modification on the nucleotide.

3. A probe comprising the nucleic acid sequence:

(SEQ ID NO: 5)
5'-CGCCTGTGAACTTTATTGGCG-3'.

4. A combination of primers and probe, wherein the primers comprise the following sequences

```
                                           (SEQ ID NO: 3)
5'-GACTCGATATCGAGTCTTTCCACmCGAAATACmCmGmCmCmA-3'
                                           (SEQ ID NO: 4)
5'-GACTCGATATCGAGTCTTTCCGG[mC]ATCATTATTATCTTTG[mU]
[mG][mA][mA][mC]-3',
``` wherein "m" preceding a nucleotide indicates the position of a 2' modification on the nucleotide, and a detectable probe comprising the following sequence:

```
                              (SEQ ID NO: 5)
5'-CGCCTGTGAACTTTATTGGCG-3'.
```

5. A kit comprising a nicking enzyme, dNTPs, a polymerase, a forward primer having the nucleic acid sequence:

```
                                                    (SEQ ID NO: 3)
5'-GACTCGATATCGAGTCTTTCCAC[mC]GAAATAC[mC][mG][mC]
[mC][mA]-3'
``` and a reverse primer having the nucleic acid sequence:

```
                                                    (SEQ ID NO: 4 )
5'-GACTCGATATCGAGTCTTTCCGG[mC]ATCATTATTATCTTTG[mU]
[mG][mA][mA][mC]-3',
``` wherein "m" preceding a nucleotide indicates the position of a 2' modification on the nucleotide, and a detectable probe comprising the following sequence:

```
                              (SEQ ID NO: 5)
5'-CGCCTGTGAACTTTATTGGCG-3'.
```

* * * * *